US009227089B1

(12) United States Patent
Greco et al.

(10) Patent No.: US 9,227,089 B1
(45) Date of Patent: Jan. 5, 2016

(54) SKIN TREATMENT FOR PROMOTING HAIR GROWTH

(75) Inventors: Joseph F. Greco, Sarasota, FL (US); Robert J. Brandt, Fort Myers, FL (US)

(73) Assignee: PGFX PATENT HOLDINGS, LLC, West Monroe, LA (US)

( * ) Notice: Subject to any disclaimer, the term of this patent is extended or adjusted under 35 U.S.C. 154(b) by 604 days.

(21) Appl. No.: 12/657,115

(22) Filed: Jan. 14, 2010

Related U.S. Application Data

(60) Provisional application No. 61/205,045, filed on Jan. 14, 2009.

(51) Int. Cl.
*A61K 38/00* (2006.01)
*A61Q 7/00* (2006.01)
*A61K 35/19* (2015.01)

(52) U.S. Cl.
CPC .. *A61Q 7/00* (2013.01); *A61K 35/19* (2013.01)

(58) Field of Classification Search
None
See application file for complete search history.

(56) References Cited

U.S. PATENT DOCUMENTS

| | | | |
|---|---|---|---|
| 4,957,742 A | 9/1990 | Knighton | |
| 5,165,938 A | 11/1992 | Knighton | |
| 5,178,883 A | 1/1993 | Knighton | |
| 5,599,558 A | 2/1997 | Gordinier et al. | |
| 6,284,285 B1 | 9/2001 | Weis-Fogh | |
| 6,303,112 B1 | 10/2001 | Worden | |
| 6,649,072 B2 | 11/2003 | Brandt et al. | |
| 6,811,777 B2 | 11/2004 | Mishra | |
| 7,011,852 B2 | 3/2006 | Sukavaneshvar et al. | |
| 7,112,342 B2 | 9/2006 | Worden | |
| 7,314,617 B2 | 1/2008 | Mishra | |
| 8,172,868 B2 * | 5/2012 | Eastman | 606/186 |
| 2003/0007957 A1 | 1/2003 | Britton et al. | |
| 2003/0198687 A1 | 10/2003 | Bennett et al. | |
| 2006/0057224 A1 | 3/2006 | Hynes | |
| 2007/0258956 A1 | 11/2007 | Higgins et al. | |
| 2007/0280959 A1 | 12/2007 | Meury et al. | |
| 2008/0193424 A1 | 8/2008 | McKale et al. | |
| 2008/0248083 A1 | 10/2008 | Mishra | |

OTHER PUBLICATIONS

Uebel et al. Plast Reconstr Surg 2006;118:1458-68.*
Kakudo et al. Plast Reconstr Surg 2008; 122:1352-60.*
Takakura et al. J Invest Dermatol 1996;107:770-7.*
Anitua et al. J Biomed Mater Res Part B: Appl Biomater 2008; 84B:415-21.*
D. Fernandes, "Minimally Invasive Percutaneous Collagen Induction", J Oral Maxillofac Surg Clin North Am. 2005, 17:51-63.
D. S. Orentreich et al., "Subcutaneous Incision-less (Subcision) Surgery for the Correction for Depressed Scars and Wrinkles", Dermotol Surg, 1995, 21:543-549.
A. Camirand et al., "Needle Dermabrasion", Aesthetic Plast Surg. 1997, 21:48-51.
Schwartz et al., "Reflections about Collagen-Induction-Therapy (CIT)—A Hypothesis for the Mechanism of Action of CIT using Micro-Needles", downloaded from http://www.dermaroller.de/CITfindings.HTM, 1st edition Feb. 2006, 2nd revision Jan. 2007.
R. Clark et al., "Synergistic Signaling from Extra Cellular Matrix-Growth Factor Complexes", Journal of Investigative Dermatology (2008), 128, 1354-1355.
V. Declair, "The Importance of Growth Factors in Wound Healing", Ostomy Wound Manager, 45, 64-68 (1999).
Y. Choi and E. Fuchs, "TGF-beta and Retnoic Acid Regulation of Growth and Modifiers of Differentiation Human Epidermal Cells", E., Crell regal. 1, 791-809 (1990).
R. Ross, "Platelet-Derived Growth Factor", Am Rev. Med 38, 71-79 (1986).
G. F. Pierce, T. A. Mustoe, J. Lingelbach, V.R. Masakowski, P.P. Gramates, T.F. Deuel, "Transforming Growth Factor B Reverses the Glucocorticoid-induced Wound Healing Defect in Rats: Possible Regulaton in Microphages by Platelet-Derived Growth Factor", Proc. Natl. Acad. Sci., 86, 2229-2233 (1989).
N. Takakura, H. Yoshida, T. Kunisada, S. Nishikawa, "Involvement of Platelet Derived Growth Factor Receptor-a in Hair Canal Formation" Journal of Investigative Dermatology, (1996), 107, 770-777.
K. Yano et al., "Control of Hair Growth and Follicle Size by VEGF-mediated Angiogenesis", J Clin Invest, Feb. 2001, vol. 107, No. 4, 409-417.
Hollier et al. "Substrate-Bound Insulin-Like Growth Factor (IGF)-I-IGF-Binding Protein-Vitronectin-Stimulated Breast Cell Migration is Enhanced by Coactivation of the Phosphatidylinositide 3-Kinase/AKT Pathway by αv-Integrins and the IGF-I Receptor".
J. Greco et al., "Our Preliminary Experience and Extended Applications for the Use of Autologous Platelet Rich Plasma in Hair Transplant Surgery", Hair Transplant Forum International, Jul.-Aug. 2007, pp. 131-132.
C. A. Carter, D. G. Jolly, C. E. Worden, D. G. Hendren, C.J.M. Kane, ,"Plate-rich Plasma Gel Promotes Differentiation and Regeneration during Equine Wound Healing", Experimental and Molecular Pathology, 74 (2003) at 244-255.
Paus, "Do We Need Hair Follicle Stem Cells and Hair Follicle Neogenesis to Cure Common Hair Loss Disorder?", Hair Transplant Forum International, May Jun. 2008, vol. 18, No. 3, 88-90.
Hopkin, "Skin's Own Cells Could Beat Baldness", Nature, May 16, 2007, doi:10.1038.

(Continued)

*Primary Examiner* — Janice Li
(74) *Attorney, Agent, or Firm* — Price & Adams, P.C.

(57) ABSTRACT

A volume of platelet-rich blood product is obtained from a volume of anti-coagulated blood to prepare a composition for promoting the growth of hair follicles within skin. A portion of the skin is traumatized to form a treatment area in which stem cells within the hair follicles are activated. A protein matrix is formed from the platelet-rich blood product composition to entrap growth factors. The platelet-rich blood product composition is infused into the treatment area to form a complex between the protein matrix and the growth factors so that the stem cells attach to the complex and proliferate within the hair follicles.

7 Claims, 12 Drawing Sheets

(56) References Cited

OTHER PUBLICATIONS

Ito et al., "Wnt-Dependent de novo Hair Follicle Regeneration in Adult Mouse Skin After Wounding", Nature International Weekly Journal of Science May 17, 2007, doi: 10.1038.

Robert E. Marx, "Platelet-Rich Plasma: Evidence to Support Its Use", Journal Oral Maxillofacial Surgery, 2004, vol. 62, pp. 489-496.

Ohyama et al. "Characterization and Isolation of Stem Cell-Enriched Human Hair Follicle Bulge Cells", The Journal of Clinical Investigation, Jan. 4, 2006, vol. 116, issue 1, pp. 249-260.

* cited by examiner

SKIN TREATMENT FOR PROMOTING HAIR GROWTH

BACKGROUND OF THE INVENTION

1. Field of the Invention

This invention relates to a skin treatment and, more particularly, to an apparatus and method for treating skin to promote hair growth.

2. Description of the Related Art

Certain skin treatments are directed to skin rejuvenation, such as micro needling. The earliest form of micro needling, acupuncture, traces its roots to the Chinese centuries ago. A French skin rejuvenation technique, called nappage, has been used within the past fifty years. Nappage is another form of micro needling in which micro incisions are made into the skin placing a drop of vitamins, minerals and anti-oxidants to replace depleted cellular levels.

A major advantage provided by micro needling is the preservation of the epidermis, the protective layer of the skin. The publication entitled "Minimally Invasive Percutaneous Collagen Induction" by D. Fernandes, J Oral Maxillofac Surg Clin North Am. 2005 at 17:51-63, discloses the benefits of preserving the epidermis.

The publication entitled "Subcutaneous Incision-less (Subcision) Surgery for the Correction for Depressed Scars and Wrinkles" by D. S. Orentreich et al., Dermotol Surg, 1995, 21:543-549, discloses a skin treatment in which subcision with a needle is used to treat wrinkles near the lip lines.

The publication entitled "Needle Dermabrasion" by A. Camirand et al., Aesthetic Plast Surg. 1997; 21:48-51, discloses that hypochromic facial scars become tattooed with a skin color pigment over time. The skin color pigment is replaced with melanin within one to two years. The appearance, the color, and the texture of the scars improve through micro needling.

The publication entitled "Reflections about Collagen-Induction-Therapy (CIT)—A Hypothesis for the Mechanism of Action of CIT using Micro-Needles" by Schwartz et al., 1st edition February 2006, 2nd revision January 2007, discloses new collagen and elastin formation at 6 weeks after "dry" micro needling. The term "dry microneedling" refers to microneedling in which no substance was used or infused into the skin. The study demonstrated a substantial increase in new collagen fibers. The fibers were only found at the corium not deeper than 0.5 mm to 0.6 mm. Even though 1.5 mm needles were used, no new collagen fibers could be found in the sub dermal layer illustrating no benefit to using longer more invasive needles. The study also evaluated the penetration forces and needle length.

Other types of skin treatments are directed to treating hair loss. Hair loss including androgenetic alopecia, also known as male-pattern or female-pattern hair loss, represents approximately fifty percent of cases involving hair loss in the United States. Hair loss may also be caused by environmental and genetic factors unrelated to androgens including alopecia greata, permanent alopecia, anagen effluvium, lichen planopilaris and discoid lupus erythematosus.

Current Food and Drug Administration (FDA) approved skin treatments for hair loss include two pharmaceutical treatments and low level light or "cold laser" therapy. Pharmaceuticals used in the treatment of androgenetic alopecia stimulate existing hair follicles to produce thicker hair and prevent hair thinning. The pharmaceutical treatments include topical minoxidil (sold under the trademark Rogaine® by Pfizer) and oral Finasteride (sold under the trademark Propecia® by Merck). Humans are born with a finite number of approximately 100,000 terminal hair follicles on the scalp.

The existing pharmaceutical treatments inhibit the effects of androgens. Individuals who are genetically susceptible to the effects of androgens experience shortened hair growth cycles, which manifest in thinning and bitemporal recession of hair.

Both pharmaceutical treatments attack the effects of dihydrotestosterone. However, neither drug restores all the hair. Neither treatment produces new follicles. Both treatments require prolonged usage of the drug, and if treatment is stopped, any benefits gained will be lost. In such instances, the hair thickness regresses to pre-treatment levels.

Reversible side effects are associated with the use of these androgen inhibitors. These side effects include decreased libido, erectile dysfunction, and dermatologic discomfort.

Other modalities for treating hair loss include in vivo hair transplantation whereby donor hair follicles from areas of the scalp that are insensitive to the effects of androgens are transplanted to areas experiencing irregular hair follicle cycling or areas with few hair follicles.

Hair transplantation can be assisted through the use of growth factors. Growth factors act in the bulge area of a hair shaft, below the sebaceous gland where stem cells are found. Growth factors interact with cells of a matrix to activate the proliferative phase of the hair. Stem cells are more primitive and of ectodermal origin. Stem cells give origin to the epidermal cells and the sebaceous glands. Cells of the dermal papilla, which are found at the capillary base, are of mesenchymal origin. Both cells need each other and interact through the action of various growth factors to give rise to the future follicular unit.

U.S. Pat. No. 6,649,072 discloses a method for producing a mixture of platelet-rich plasma and concentrated platelet-poor plasma. The method creates a natural protein extra cellular matrix (ECM) that entraps various growth factors (GF), which allows cells to attach and proliferate.

The publication entitled "Synergistic Signaling from Extra cellular Matrix-Growth Factor Complexes" by R. Clark et al., Journal of Investigative Dermatology (2008) 128, 1354-1355. doi:10.1038/jid.2008.75, discloses that "GF-ECM complexes may well be the most effective and efficient method to stimulate cell proliferation, as well as tissue healing or regeneration."

Platelet rich plasma (platelet-rich plasma) contains several growth factors, including platelet-derived growth factors (PDGF), transforming growth factor-beta 1 (TGF-beta 1) at high levels and vascular endothelial growth factor (VEGF). When platelets are activated growth factors are released which emit chemical signals to surrounding areas multiplying the growth factors thus causing a heighten "immune response".

The main function of PDGF is to stimulate cell replication (mitogenesis) of healing capable stem cells. The publication entitled "The Importance of Growth Factors in Wound Healing" by V. Declair, Ostomy Wound Manage, 45, 64-68 (1999), discloses that growth factors are essential for the regulation of the cellular events involved in wound healing by attracting cells to the wound, stimulating proliferation, and significantly influencing matrix deposition.

The publication entitled "TGF-beta and Retnoic Acid Regulation of Growth and Modifiers of Differentiation Human Epidermal Cells" by Y. Choi and E. Fuchs, E., Crell regal. 1, 791-809 (1990), discloses that TGF-beta is extremely important because it affects most aspects of tissue wound repair, namely initiation and termination and also promotes differentiation and proliferation.

Fibroblasts are among the cells that are activated by TGF-beta. When a fibroblast is activated, the fibroblast will undergo cell division to produce collagen. Collagen deposition is responsible for plumping the skin and reversing the visible signs of aging.

The publication entitled "Platelet-Derived Growth Factor" by R. Ross, Am Rev. Med. 38, 71-79 (1986) discloses that PDGF improves dermal regeneration, acts locally to promote protein and collagen synthesis, and causes endothelial migration or angiogenesis. The publication entitled "Transforming Growth Factor B Reverses the Glucocorticoid-induced Wound Healing Defect in Rats: Possible Regulation in Microphages by Platelet-Derived Growth Factor" by G. F. Pierce, T. A. Mustoe, J. Lingelbach, V. R. Masakowski, P. P. Gramates, T. F. Deuel, Proc. Natl. Acad. Sci., 86, 2229-2233 (1989), discloses that PDGF induces the expression of TGF-beta.

The publication entitled "Involvement of Platelet Derived Growth Factor Receptor-a in Hair Canal Formation" by N. Takakura et al., Journal of Investigative Dermatology. (1996) 107, 770-777, discloses that PDGF signals are involved in epidermis-follicle interaction and dermal mesenchyme interaction. Epidermis-follicle interaction is required for hair canal formation. Dermal mesenchyme interaction is required the growth of dermal mesenchyme.

PDGF also performs other functions. The publication entitled "Platelet-Derived Growth Factor" by R. Ross, Am Rev. Med. 38, 71-79 (1986) discloses that PDGF improves dermal regeneration, acts locally to promote protein and collagen synthesis, and causes endothelial migration or angiogenesis. The publication entitled "Transforming Growth Factor B Reverses the Glucocorticoid-induced Wound Healing Defect in Rats: Possible Regulation in Microphages by Platelet-Derived Growth Factor" by G. F. Pierce, T. A. Mustoe, J. Lingelbach, V. R. Masakowski, P. P. Gramates, T. F. Deuel, Proc. Natl. Acad. Sci., 86, 2229-2233 (1989), discloses that PDGF induces the expression of TGF-beta.

The publication entitled "Involvement of Platelet Derived Growth Factor Receptor-a in Hair Canal Formation" by N. Takakura, H. Yoshida, T. Kunisada, S. Nishikawa, J. of Investigative Dermatology, (1996), 107, 770-777, discloses that PDGF signals are involved in both epidermis-follicle interaction and the dermal mesenchyme interaction required for hair canal formation and the growth of dermal mesenchyme.

The publication entitled "Control of Hair Growth and Follicle Size by VEGF-mediated Angiogenesis" by K. Yano et al., J Clin Invest, February 2001, Volume 107, Number 4, 409-417, identifies VEGF as a major mediator of hair follicle growth providing the first direct evidence of follicular revascularization. The publication discloses that improved follicle revascularization promotes hair growth, increases follicle size, and increases hair size.

The publication entitled "Substrate-Bound Insulin-Like Growth Factor (IGF)-I-IGF Binding Protein-Vitronectin-Stimulated Breast Cell Migration Is Enhanced by Coactivation of the Phosphatidy linositide 3-Kinase/AKT Pathway by v-Integrins and the IGF-I Receptor" by Z. Upton et al. discloses that vitronectin (VN) complexes with insulin-like growth factor (IGF) and IGF-binding proteins (IGFBPs) could enhance migration of human keratinocytes in vitro and possibly in vivo.

U.S. Patent Publication No. 2008/0248083 discloses an enriched platelet-containing mixture for treating injuries. The mixture is isolated from whole blood and resuspended in a small volume of plasma. The platelets are living, terminal cytoplasmic portions of marrow megakaryocytes that have no nucleus for replication and die off in 5-9 days. The platelets adhere together to form a platelet plug at an injury site and actively extrude the growth factors involved in initiating wound healing. These growth factors, also called cytokines, are small proteins each of about 25,000 Daltons molecular weight. They are stored in granules in platelets. In response to platelet to platelet aggregation or platelet to connective tissue contact, the cell membrane of the platelet is "activated" to release these alpha granules. These growth factors include PDGF, transforming growth factor beta 1 and 2 (TGF-β), fibronectin (FN), VN, fibrin and insulin-like growth factor (ILGF). These growth factors function to assist the body in repairing itself by stimulating stem cells to regenerate new tissue and by promoting vascularization.

The publication entitled "Our Experience Utilizing Autologous Platelet Rich Plasma in all Phases of Hair Transplant Surgery" by J. Greco et al., Hair Transplant Forum International, July-August, 2007, pp 131-132, discloses that platelet-rich plasma and PDGF can be used in hair transplantation surgery. The publication discloses the bathing of hair grafts in activated platelet-rich plasma to increase graft survival and yield in hair restoration surgery. The publication discloses that using platelet-rich plasma as a graft storage medium provides quicker healing.

U.S. Patent Publication No. 2007/0258956 discloses treatments for androgenetic alopecia and other forms of hair loss by inducing and expediting the growth of hair in the scalp of a patient. The disclosure includes the steps of isolating adipose-derived cells and hair follicles from the patient and implanting the combined cells and follicles into the scalp in areas requiring new growth of hair. The use of differentiated and undifferentiated adipose-derived cells with processed and grafted hair follicles for the therapeutic and cosmetic treatment of hair loss in vivo is disclosed. The use of adipose-derived cells with platelet concentrate or platelet-rich plasma is also disclosed.

U.S. Patent Publication No. 2003/0198687 discloses a method for promoting hair growth using platelet-rich plasma. The platelet enriched plasma is injected into subcutaneous tissue to promote hair growth.

U.S. Pat. No. 4,957,742 discloses a method for promoting hair growth using platelet enriched plasma. The platelet enriched plasma is applied to tissue to promote hair growth.

U.S. Pat. No. 5,178,883 discloses a method for preparing platelet enriched plasma. The platelet enriched plasma is applied to tissue to inter alia promote hair growth.

U.S. Pat. No. 5,165,938 discloses a method for preparing platelet enriched plasma. The platelet enriched plasma is applied to tissue to treat wounds.

The publication entitled "Plate-rich Plasma Gel Promotes Differentiation and Regeneration during Equine Wound Healing" by C. A. Carter, D. G. Jolly, C. E. Worden, D. G. Hendren, C. J. M. Kane, Experimental and Molecular Pathology, 74 (2003) at 244-255, discloses that wounds treated with platelet-rich plasma gel exhibit enhanced wound repair and possess more organized collagen. The use of platelet-rich plasma gel does not result in excessive disposition of connective tissue or scar formation.

U.S. Pat. Nos. 6,811,777 and 7,314,617 disclose the use of platelet-rich plasma for treating an injury. The term injury refers to any tissue damage including a wound, trauma or lesion or any tissue degeneration. In particular, the inventive platelet compositions may be used to treat incomplete repair of various connective tissues.

U.S. Patent Publication No. 2008/0193424 discloses a treatment of tissue defects using a therapeutic composition. The composition may include a mixture of platelet-rich plasma and concentrated platelet poor plasma. The composition is used to treat traumatized regions of the body.

U.S. Patent Publication No. 2007/0280959 discloses a new use for platelets or platelet rich plasma that is obtained by disruption of membranes for the preparation of an agent for the treatment of bone, cartilage or skin.

U.S. Patent Publication No. 2006/0057224 discloses a method for treating an open wound using platelet poor plasma and platelet rich plasma as a sealant.

U.S. Patent Publication No. 2003/0007957 discloses a method for treating wounds in traumatized areas using platelet-rich plasma with a structural matrix.

U.S. Pat. Nos. 6,303,112 and 7,112,342 disclose the use of an improved platelet gel wound healant for treating traumatized regions of the body. The improved wound healant includes a therapeutically effective amount of activated growth factors and ascorbic acid.

U.S. Pat. No. 7,011,852 discloses a method for separating, retrieving and concentrating platelets from whole blood relying on aggregation of the platelets followed by filtration. The purpose of this method is to prepare a platelet-rich plasma composition for treating injuries.

U.S. Pat. No. 6,284,285 discloses a method for obtaining fibrinogen and other growth factors to form a platelet-rich plasma composition. The platelet-rich plasma composition is used to promote tissue repair.

U.S. Pat. No. 5,599,558 discloses a method of making platelet releasate product. The platelet releasate product has many applications, including for the promotion of hair growth.

The publication entitled "Platelet Rich Plasma Gel Promotes Differentiation and Regeneration during Equine Wound Healing" by C. Carter, Experimental and Molecular Pathology 74; 244-55 (2003), discloses that platelet-rich concentrate enhances wound repair, decreases scar collagen, enhances Type III collagen, and increases wound tensile strength. Accordingly, there is a need to provide an improved treatment that promotes hair growth and rejuvenates skin.

SUMMARY OF THE INVENTION

In accordance with the present invention there is provided a method for promoting hair growth within skin that includes a plurality of hair follicles. A volume of a platelet-rich blood product composition is obtained from a volume of anti-coagulated blood. A portion of the skin is traumatized within a treatment area to activate stem cells within the hair follicles to form a quantity of activated stem cells within the treatment area. A protein matrix is formed from the platelet-rich blood product composition to entrap growth factors therein. The platelet-rich blood product composition is infused into the treatment area to form a complex between the protein matrix and the growth factors so that the quantity of activated stem cells attaches to the complex and proliferates within the hair follicles.

Further in accordance with the present invention, there is provided a kit for treating skin tissues to promote hair growth. The skin tissues are traumatized to activate stem cells to form a quantity of activated stem cells within hair follicles in the skin tissues. A volume of platelet-rich blood product composition to infuse into the skin tissues to form complexes between a protein matrix and growth factors so that the quantity of activated stem cells attaches to the complexes and proliferates within the skin tissues is provided. A container holds the volume of platelet-rich blood product composition.

Further in accordance with the present invention, there is provided an apparatus for treating skin that includes an elongated member having a first opening at one end, a second opening at the other end, an internal cavity connecting the first opening to the second opening, and a fork extending therefrom. A roller is mounted for rotation within the fork. The roller has a rotating surface with a plurality of protrusions for traumatizing the skin to activate stem cells within a skin treatment area to form activated stem cells. A plunger member inserts into the first opening to form a chamber for holding a protein matrix forming platelet-rich blood product composition within the internal cavity. The plunger member moves within the cavity to decrease the volume of the chamber and force the platelet-rich blood product composition through the second opening to infuse the platelet-rich blood product composition into the treatment area to proliferate the activated stem cells therein.

Further in accordance with the present invention, there is provided a method for treating skin. An elongated member having a container for holding a platelet-rich blood product composition at one end and a roller extending from the opposite end is provided. A complex is formed between a protein matrix and growth factors within the platelet-rich blood product composition. The roller is rotated to traumatize a portion of the skin to activate stem cells within a treatment area. The platelet-rich blood product composition is dispensed from the container to infuse the platelet-rich blood product composition into the treatment area so that the complex interacts with the activated stem cells in the treatment area.

Further in accordance with the present invention, there is provided a method for promoting hair growth within skin that includes a plurality of hair follicles. An elongated member having a container for holding a platelet-rich blood product composition at one end and a roller extending from the opposite end is provided. A complex is formed between a protein matrix and growth factors within the platelet-rich blood product composition. The roller is rotated to traumatize a portion of the skin to form a quantity of activated stem cells within the hair follicles within the treatment area. The platelet-rich blood product composition is dispensed from the container to infuse the platelet-rich blood product composition into the treatment area so that the complex interacts with the quantity of activated stem cells within the hair follicles within the treatment area.

A principal object of the present invention is to provide a treatment for hair loss.

Another object of the present invention is to provide a method for infusing a platelet-rich blood product composition into skin to promote hair growth.

Another object of the present invention is to provide an apparatus that traumatizes a treatment area with a roller and dispenses a platelet-rich blood product composition onto the treatment area.

A further object of the present invention is to provide a method for infusing a platelet-rich blood product composition into skin to rejuvenate skin.

These and other objects of the present invention will be more completely described and disclosed in the following specification, accompanying drawings, and appended claims.

DESCRIPTION OF THE PREFERRED EMBODIMENTS

Figure 1:
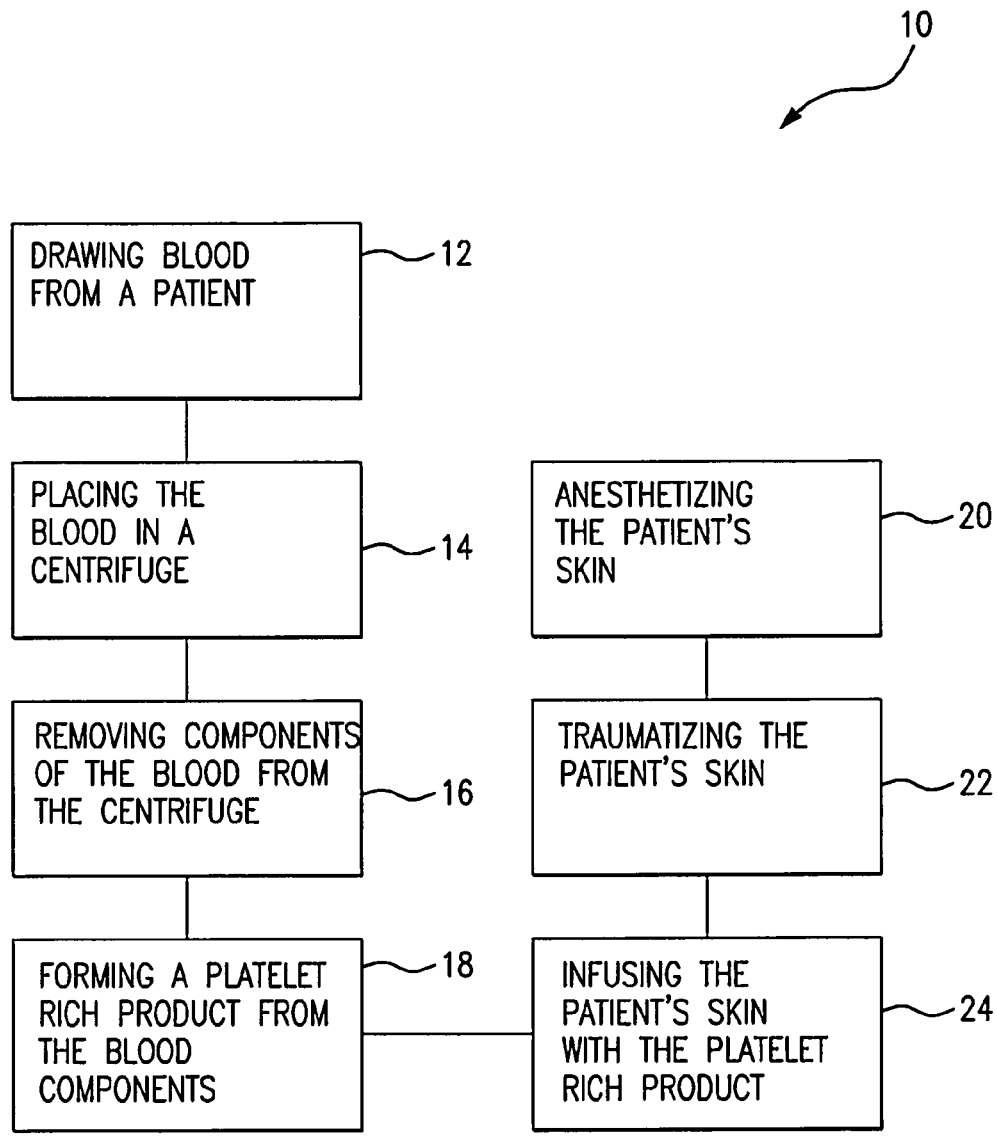
FIG. 1 is a block diagram for a skin treatment method for promoting hair growth that includes traumatizing a treatment area and infusing a platelet-rich blood product composition into the treatment area.

Referring to the drawings and, particularly, to FIG. 1, there is shown a series of steps generally designated by the numeral 10 that illustrate a method for treating and rejuvenating skin to promote hair growth using a platelet-rich blood product composition. The methods and apparatus of the present invention are used to create new hair follicles and new hair on any region, such as the scalp, for suitable subjects, including mammals and, in particular, humans. The method has a positive effect in reversing miniaturization in androgenic alopecia. The method is also suitable for stimulating hair growth in alopecia areata patients.

The method 10 includes a series of steps 12, 14, 16, 18 directed to processing blood from a patient to obtain the platelet-rich blood product composition. The method 10 also includes a series of steps 20, 22 directed to traumatizing a portion of the skin on the patient and a step 24 directed to infusing the composition into the traumatized region.

The series of steps 12, 14, 16, 18 involves processing a blood sample to produce a platelet-rich blood product composition. The first step 12 involves obtaining a volume of blood from a patient through conventional blood drawing techniques to produce the blood sample. The blood is mixed with an anti-coagulant, as indicated by step 14, within a container. The container is placed in a centrifuge.

In the centrifuge, the anticoagulated blood is separated into a platelet poor fraction, a buffy coat, and a layer of red blood cells to form various blood components for mixing. Optionally, the anticoagulated blood fractions are subjected to additional separation steps within the centrifuge.

The blood fractions are removed from the centrifuge, as indicated in step 16. After removal, the blood fractions are mixed to form the platelet-rich blood product composition (step 18) for use in the infusing step 24. Preferably, the platelet-rich blood product composition is an autologous platelet-rich plasma product to minimize side effects and complications from the treatment.

As shown in FIG. 1, the method 10 involves traumatizing a portion of the skin of a patient, as indicated in step 22, which activates stem cells within hair follicles in the treatment area to form a quantity of activated stem cells. Next, the treatment area is infused with a platelet-rich blood product composition, as indicated in step 24. The traumatizing step 22 and the infusion step 24 cause dormant stem cells in the bulge region of hair follicles to reverse and to enter a growth phase.

The platelet-rich blood product composition has the ability to form a natural protein ECM that entraps various GF allowing cells to attach and proliferate. The natural protein matrix maintains the growth factors in the area longer and works synergistically for revascularization and proliferation of new cells and some ECM-GF complexes. The ECM-GF complexes are an effective and efficient method for stimulating cell proliferation, as well as tissue healing or regeneration.

Referring to FIG. 1, the traumatizing step 22 is performed using any suitable instrument for traumatizing skin that activates stem cells within hair follicles in a treatment area. Suitable instruments include mechanical instruments, such as a mechanical incision trauma instrument. Suitable instruments also include optical instruments, such as a laser, a light source, or a photo therapy instrument. Suitable instruments also include ultrasonic instruments.

Suitable traumatizing methods also include chemical methods, which are performed by dispensing chemicals from a suitable dispenser. Chemical methods include methods that use liquids, gels, creams, gases, vapors, or naturopathic chemicals.

Other suitable methods for traumatizing the treatment area include electroportation, which is provided by a suitable electroportation instrument, heating of the skin, or cooling of the skin. Suitable traumatizing instruments also include epidermal or dermal abrasion instruments. Preferably, the stem cells are activated using a micro needling roller to traumatize the treatment area.

Micro needling increases the remolding of the skin by creating thousands of microscopic channels thru the skin, to increase the formation of new tissue by activating a wound healing cascade (hemostasis-inflammation-proliferation-tissue remodeling) within the body. The micro-channeling causes the release of growth factors that promote scar-less healing and the deposition of normal woven collagen rather than scar collagen.

Suitable micro needling systems include various delivery systems. The preferred micro needling system is the 5 mm MTS Roller™ provided by Clinical Resolutions Laboratory, Inc. The system creates thousands of channels thru the epidermis in a safe, cost effective, and simple manner. Needle depth is pre set and cannot penetrate deeper than the length of the needles. The rollers are FDA approved.

Referring to FIG. 1, the infusing step 24 is performed through any suitable infusion method or technique for infusing the blood product composition. Suitable infusion methods include injection, micro needling, ultrasound, electroportation, or through any suitable transdermal device, such as patches or dressings. Other suitable infusion methods include vacuum assisted methods, mechanical methods, or chemical methods.

Suitable chemical methods for infusing the blood product composition include methods that use minerals, natural carrier agents in solution, creams, lotions, gels, or natruropathic chemicals. An example of a mineral carrier is a nanodiamond carrier. Nanodiamonds are effective at delivering chemotherapy drugs to cells without the negative effects associated with current drug delivery agents.

The blood product composition is applied topically in a clotted fashion onto the treatment area in the infusing step 24. The topical application of the blood product composition prevents the composition from re-entering the circulatory system of the body. The topical application of the blood product composition provides for safety when clot accelerators such as bovine thrombin are used or when platelet-rich plasma is added to other materials, such as bovine collagen, gel foam, PLA-PGLA constructs, and other similar materials.

Referring now to FIGS. 1-4, the platelet-rich blood product composition is obtained from a suitable sample of blood. The first step 12 involves drawing 50 cc of blood from the patient. The blood is centrifuged for 10 minutes, in step 14, until the platelets are separated from the remaining blood. The platelets carry growth factors. Preferably, the blood is obtained from the patient who is being treated (i.e. an autologous blood sample). The use of an autologous blood sample is safer and avoids the risk of transmissible diseases such as HIV, Hepatitis B, C, or D, and other blood borne pathogens.

The centrifuged blood includes a layer of platelet poor plasma, a layer of red blood cells, and a white layer (i.e. a buffy coat) between. The white layer includes the aggregated platelets of concentrated platelets. After the blood has been separated in the layers, the white layer is drawn off, and the buffy coat is gently washed to allow extraction of the platelet rich plasma. The extracted sample includes a concentration of platelets and growth factors times ten.

Figure 2:
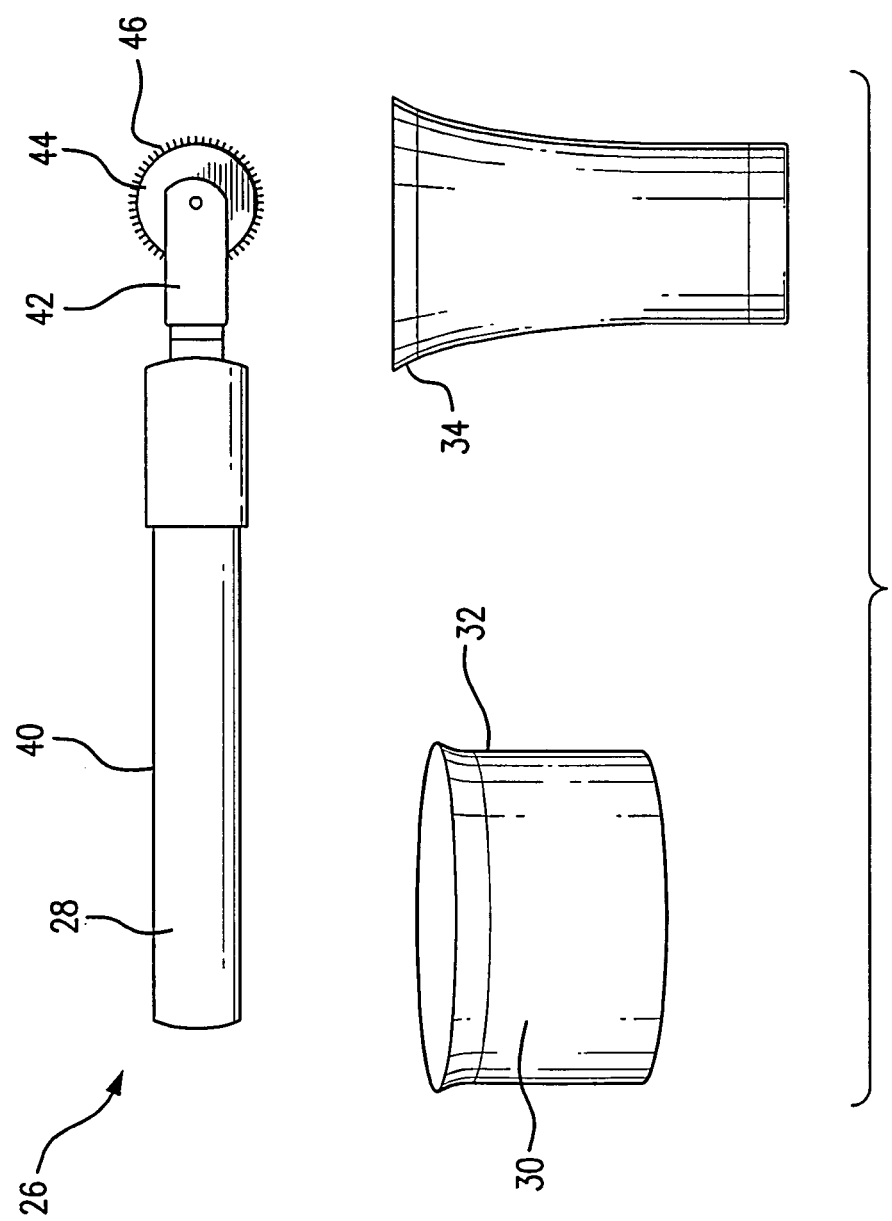
FIG. 2 is a perspective view of a skin treatment kit.
Figure 3:
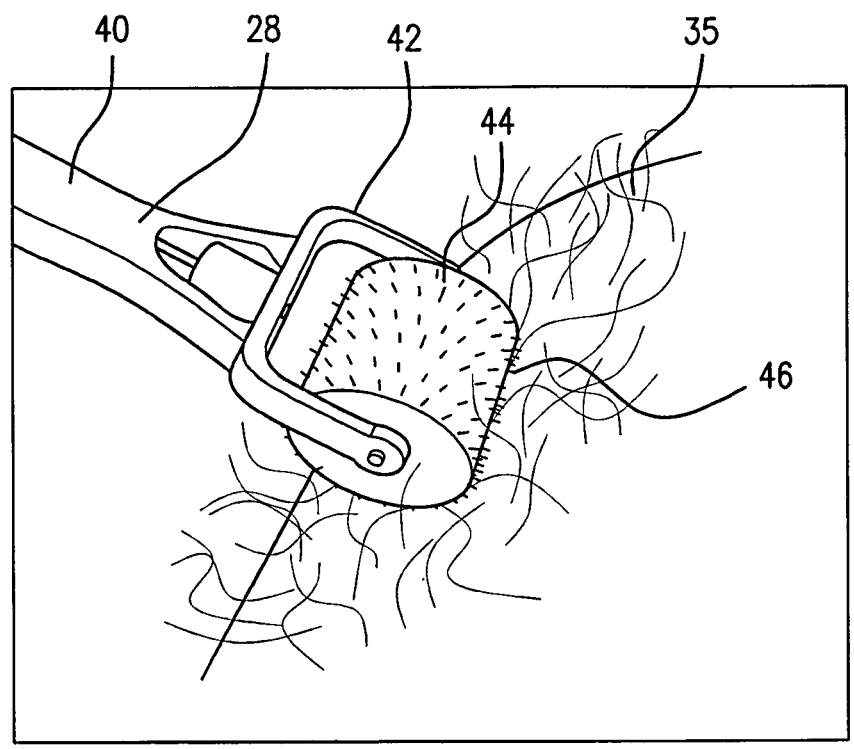
FIG. 3 is a perspective view of a micro needling roller traumatizing skin.
Figure 4:
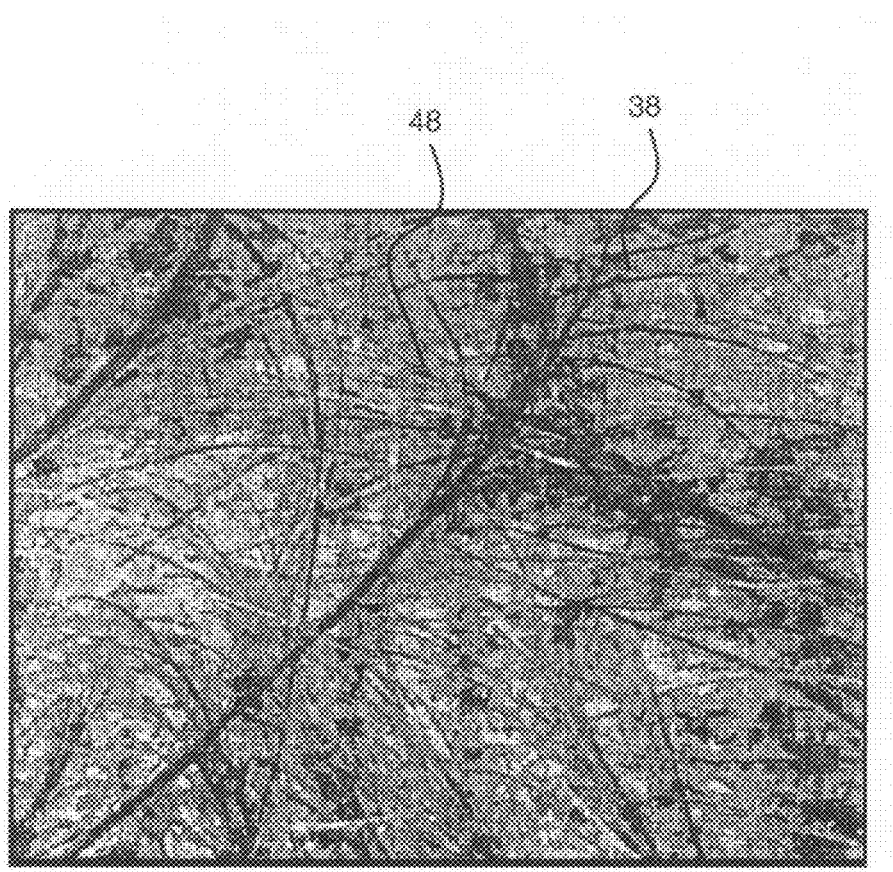
FIG. 4 is a perspective view of a portion of skin after trauma.

As illustrated in FIGS. 2-4, a skin treatment kit 26 is assembled after the platelet-rich blood product composition is obtained from a volume of blood. The kit 26 includes a suitable traumatizing instrument 28 for traumatizing the treatment area, a quantity 30 of the platelet-rich blood product composition, a container 32 for holding the platelet-rich blood product composition, and a tube 34 of anesthetizing agent.

As shown in FIGS. 3-4, a patient is prepared for treatment in step 20, as indicated in FIG. 1. The preparation involves applying the anesthetizing agent 34 to the portion of the skin 36 to reduce or eliminate pain that is caused by the traumatizing step 22. The selection of the anesthetizing agent 34 is not critical.

The anesthetized region is traumatized using the traumatizing instrument 28, as indicated in step 22 of FIG. 1, to form a traumatized region or treatment area 38. Preferably, the traumatizing instrument 28, as illustrated in FIG. 2, is a micro needling roller having an elongated handle 40, a fork 42, and a roller 44 mounted within the fork 42. The roller 44 includes a plurality of micro needles 46 that traumatize the patient's skin 36 and, optionally, infuse the platelet rich blood product composition into the treatment area 38.

As shown in FIGS. 3-4, the microneedles 46 on the roller 44 form a plurality of wounds 48 within the treatment area 38. The formation of wounds 48 activates the immune system of the patient to activate stem cells within the traumatized region or treatment area 38. The wounds 48 are infused with the platelet-rich blood product composition during the infusing step 24 shown in FIG. 1, so that the ECM-GF complexes within the blood product composition cooperate with the activated stem cells to grow new hair and rejuvenate skin. Preferably, the traumatized region or treatment area 38 is located on the scalp when the treatment is directed to promoting hair growth or reducing hair loss.

Figure 5:
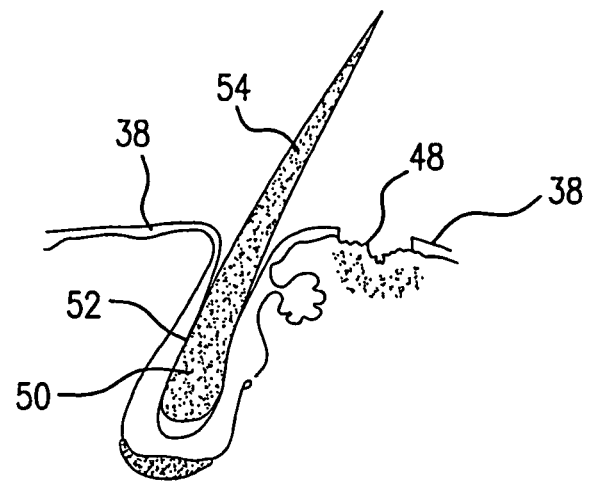
FIG. 5 is a view in side elevation of the activation stem cells in a traumatized skin region.
Figure 6:
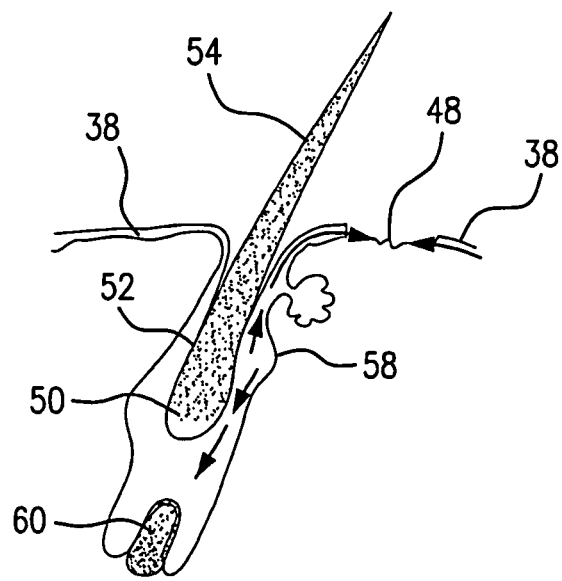
FIG. 6 is a view in side elevation of Stat3-dependent keratinocyte migration brought about by the traumatizing step shown in FIG. 5.
Figure 7:
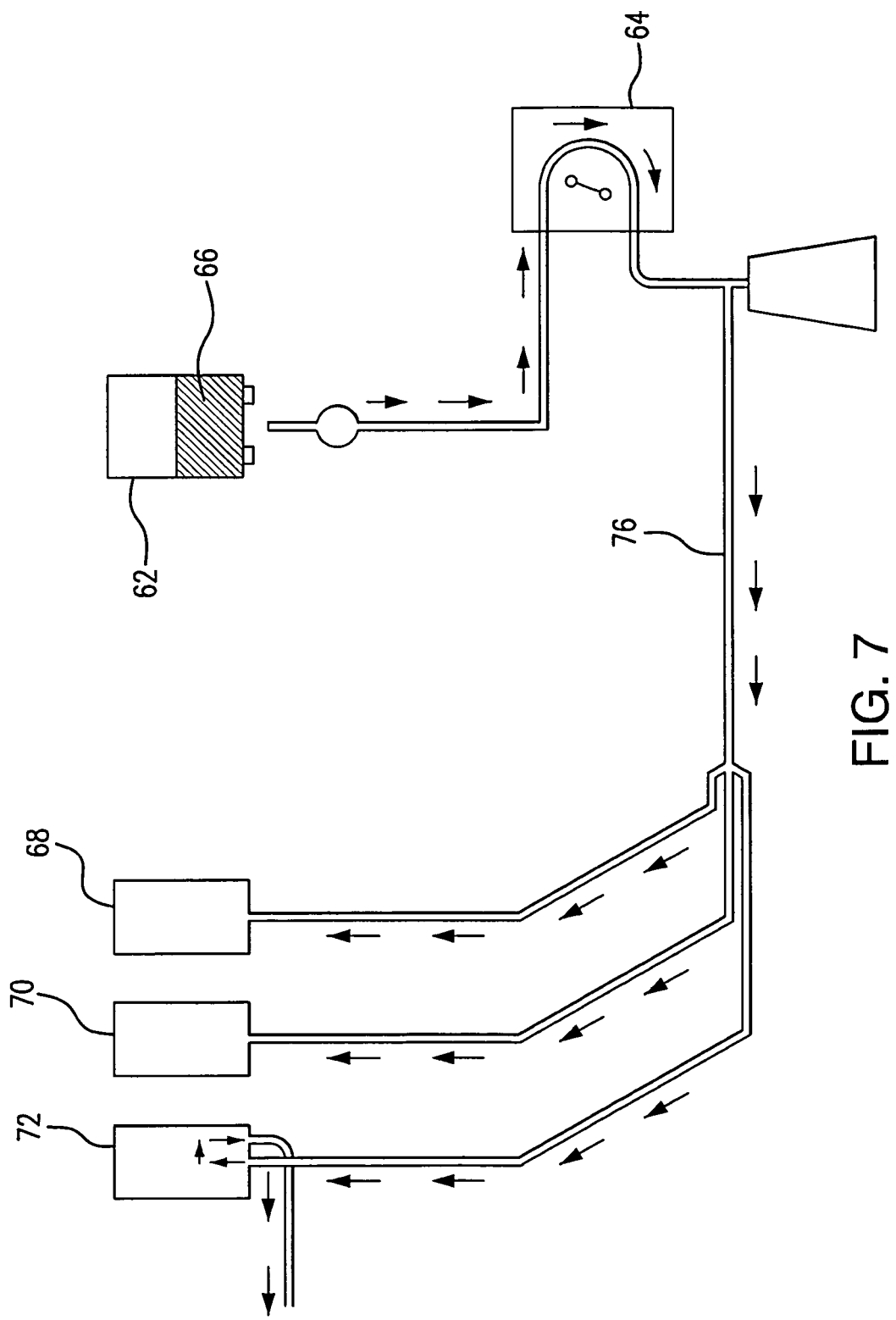
FIG. 7 is a schematic diagram for the first part of a process for obtaining an autologous platelet rich blood composition.
Figure 8:
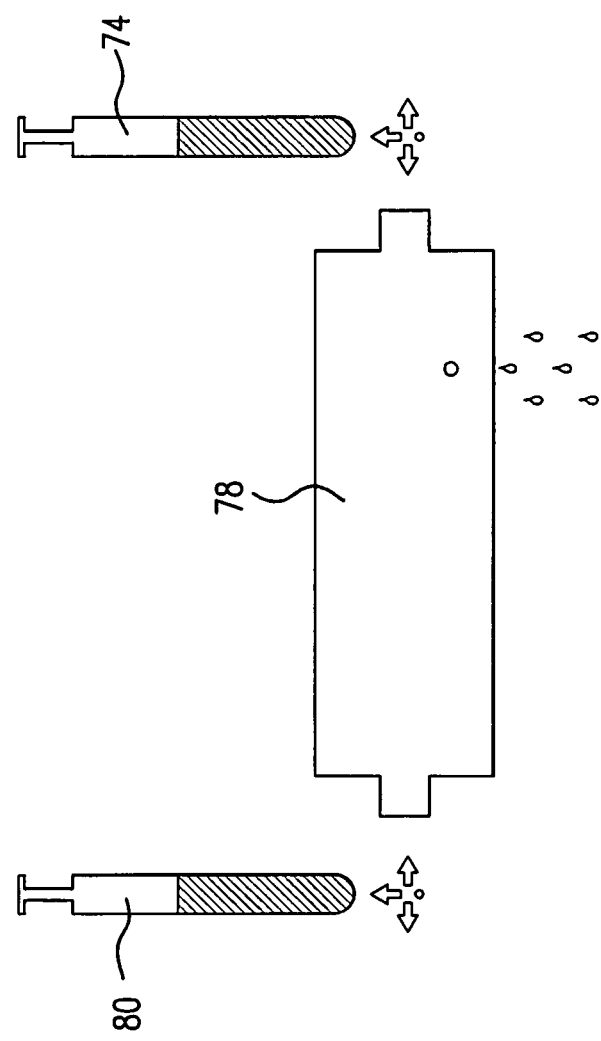
FIG. 8 is a schematic diagram for the second part of the process for obtaining an autologous platelet rich blood composition shown in FIG. 7.

Referring now to FIGS. 5-6, the mechanism for activating stem cells 50 within the traumatized region 38 is illustrated. The stem cells 50 are located on a bulge region 52 on a hair follicle 54. Traumatizing the region 38 creates an affected zone that stimulates Stat3-dependent keratinocyte migration from a source 58 to the wound 48 and to dermal papilla 60 located below the hair follicle bulge region 52.

The Stat3-dependent keratinocyte migration also activates the stem cells 50 within the bulge region 52. This epithelial-mesenchymal interaction between keratinocyte stem cells and dermal papilla cells is crucial for the normal development of the hair follicle, as well as during hair cycle.

The traumatizing step 22 triggers an immune response within the body. The traumatizing step 22 also activates the stem cells 50 in the bulge area 52 of the follicle 54 into a horizontal migration of cells, which proliferate new cells in the area of trauma and, secondarily, promotes a vertical migration of cells, thereby initiating an early progression into the anagen (growth) phase.

Miniaturized hair follicles 54, including follicles that have been miniaturized beyond recognition by the naked eye, have the potential of retransformation and the ability to generate large shafts. The stem cells 50 within such follicles 54 provide the follicles 54 with the ability to regenerate. Vellus hair follicles essentially have the same complement of epithelial hair follicle stem cells in the bulge region on their outer root sheath as large terminal ones.

Growth factors are present in the bulge area 52 of the hair shaft 54 below the sebaceous gland. The growth factors interact with cells of the matrix, which activates the proliferative phase of the hair. Stem cells are more primitive and of ectodermal origin. Stem cells originate the epidermal cells and the sebaceous glands. Dermal papilla cells, which are found at the capillary base, are of mesenchymal origin. Stem cells and dermal papilla cells cooperate and interact through the action of various growth factors to form future follicular units.

Referring now to FIGS. 7-10, the method for preparing a suitable platelet-rich blood product composition is shown. The method corresponds to the method disclosed in U.S. Pat. No. 6,649,072, which is incorporated herein by reference.

The first step in preparing the composition involves obtaining about 200 to 500 milliliters of whole blood from a patient via conventional phlebotomization techniques. Preferably, the blood B is added to a collection container 62 (such as a conventional IV bag, for example) containing an anticoagulant, such as citrate phosphate dextrose adenine solution (CPDA), for example.

The blood is then channeled, via a pump 64, from the container 62 into a centrifuge bowl 66 which is spinning at about 5,000 to 6,000 RPM's, more preferably about 5,600 RPM's (i.e. a "hard" spin). During the centrifugation process, the blood is separated into three distinct components which, in turn, are eventually diverted into separated containers or bags 68, 70, 72. The first layer or component to be "spun off" is the "platelet poor plasma" component (hereinafter the "platelet-poor plasma component"), which is the lightest in density and composed primarily of plasma proteins. Preferably about 60 to 120 ml of the platelet-poor plasma component is removed from the bowl 66 via a syringe 74 and set aside for further processing. The second separated layer is the buffy coat, which is largely composed of platelets and white blood cells, and finally the bottom layer is composed of packed red blood cells.

When the buffy coat is first detected during centrifugation, the centrifugal speed is reduced to about 2,000 to 3,000 RPM, more preferably about 2,400 RPM. At this point, the centrifuge is placed in "stand-by" mode for about 2 minutes, during which time the introduction of whole blood is stopped. This "soft" spin allows the maximum number of platelets remaining in the red blood cell layer to separate and migrate into the buffy coat layer, thereby producing a concentrated platelet rich plasma component.

The platelet-rich plasma component is then diverted into a separate container 70 as additional whole blood is manually introduced into the centrifuge every two to three seconds. The introduction of additional whole blood into the centrifuge bowl 66 serves to push the resulting PRP component out of the bowl and through the tubing 76 leading to the respective collection container 70 for the PRP component. This aspect of the process serves to "milk" out the platelet fraction through the buffy coat, thereby extracting the maximum amount of platelets from the patient's blood. This "milking" step is continued until about the first millimeter of packed red blood cells are entered, as evidenced by the detection of a "flame" entering the plasma already collected in the platelet-rich plasma collection container. For example, when a 55-ml centrifuge bowl is employed during the process, an additional 5 ml of blood is added after the "flame" is detected (for a 125 ml bowl, an additional 10 ml of blood is added upon detection of the "flame").

Once the platelet-rich plasma component has been removed, the remaining platelet-poor plasma component and red blood cells are diverted into a second collection bag 68 for holding and reprocessing. By reprocessing the remaining platelet-poor plasma/red blood cell components (i.e. centrifugal separation at 5,000 to 6,000 RPMs, followed by centrifugal separation between 2,400 to 3,000 RPMs, followed by the "milking" process as described above), the maximum amount of platelets may be removed. After the platelet-poor plasma/red blood cell component has been reprocessed a second time, the remaining red blood cells and platelet-poor plasma component are collected in the separate collection bag 68, for future re-infusion into a patient.

The platelet-poor plasma component originally extracted from the whole blood during the first centrifugal separation is processed through a hemoconcentrator 78. The hemoconcentrator 78 is any suitable device that extracts out extracellular water and reduces the volume of plasma, including hemoconcentrators that utilize membranes or membrane mimetic technology made from polysulfone, polyvinyl pyrrolidone, polyacrylimide, or other medical grade polymers.

Suitable hemoconcentrators 78 include hemoconcentrators that utilize sheet membranes, fibers, tubular fibers, hollow fibers, porous desalting beads, or other similar structures. Suitable hemoconcentrators 78 include devices that utilize insoluble beads or disks that absorb a substantial volume of water without introducing any undesirable contaminant into the plasma. Preferably, the hemoconcentrator 78 is a pediatric hemoconcentrator (shown schematically in FIG. 8), to which a negative pressure of up to 500 mm Hg has been applied (via a tumsent syringe or outside vacuum source), to extract out extracellular water, thereby reducing its volume by 5/6 while simultaneously increasing the fibrinogen levels normally found in the plasma.

During the hemoconcentrating procedure, one syringe 74 is filled with a volume of platelet-poor plasma (preferably approximately 60 ml) while a second syringe 80 remains temporarily empty. The volume of platelet-poor plasma is manually pushed through the hemoconcentrator 78 and into syringe 74. Once the platelet-poor plasma volume from the first syringe 74 is extracted, the direction of plasma flow is reversed and the platelet-poor plasma volume is pushed from syringe 80 back through the hemoconcentrator 78 and into syringe 74 again.

Figure 9:
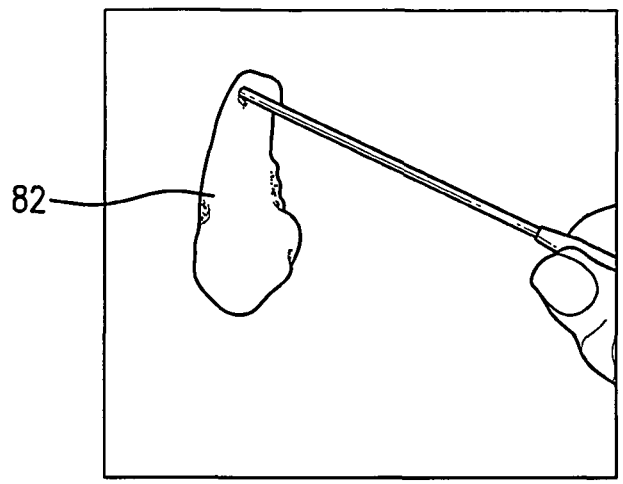
FIG. 9 is a perspective view of concentrated platelet poor plasma.

As discussed above, this process of pushing the volume of platelet-poor plasma back and forth through the concentrator in the presence of a negative pressure of up to 500 mm Hg is continued until the volume of platelet-poor plasma fraction is reduced to about 5/6. The concentrated platelet-poor plasma component 82 is shown in FIG. 9.

Figure 10:
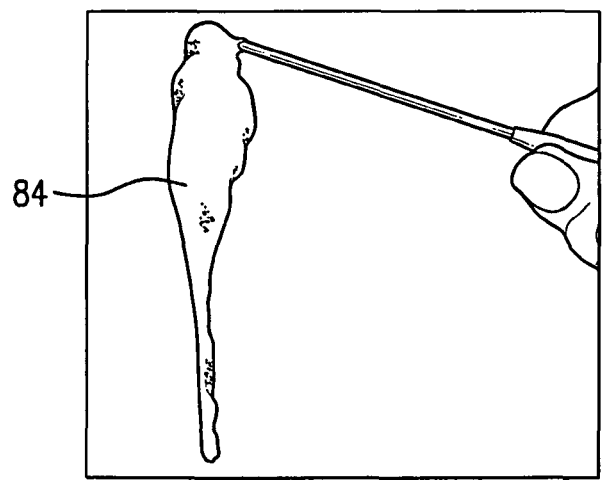
FIG. 10 is a perspective view of a mixture of concentrated platelet poor plasma with platelet rich plasma.

The resulting platelet-rich plasma and concentrated platelet-poor plasma components are then preferably combined in a ratio of 3 ml (platelet-rich plasma) to 1 ml (concentrated platelet-poor plasma) for optimal results; however, it will be recognized by the skilled artisan that blood compositions having different ratios of platelet-rich plasma to platelet-poor plasma may be employed, depending upon the intended therapeutic end use of the composition. The mixture 84 is shown in FIG. 10.

The final processed blood composition has a platelet count of between three to six times the native baseline count. For example, if a patient's platelet count is 250,000/μl, then the number of platelets in the inventive composition is within the therapeutic range of 1-1.5 million/μl.

The preferred equipment used to extract the whole blood into its separate components described herein may be any conventional centrifugation machine typically used in biomedical, and more specifically, blood processing, applications. An exemplary centrifuge is a Dideco Compact Advanced, manufactured by Dideco of Italy. A preferred hemoconcentrator is the pediatric Hemocor brand hemoconcentrator, manufactured by Minntech of Minneapolis, Minn.

Figure 11:
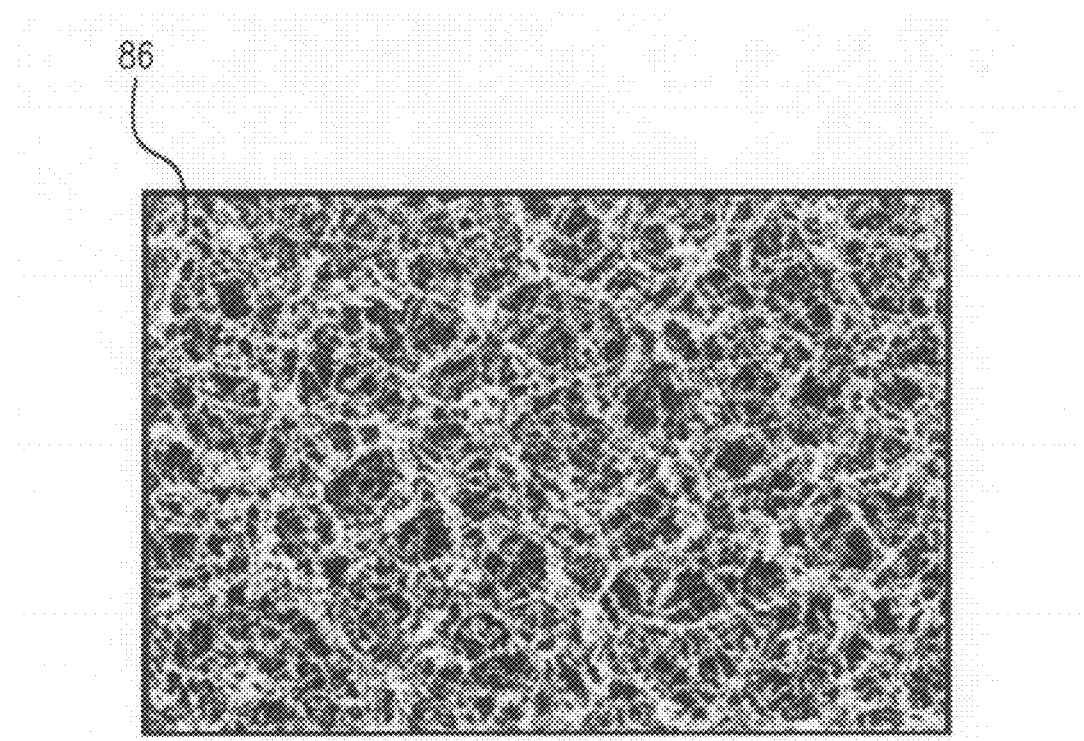
FIG. 11 is a scanning electron microscope image of a natural protein ECM.
Figure 12:
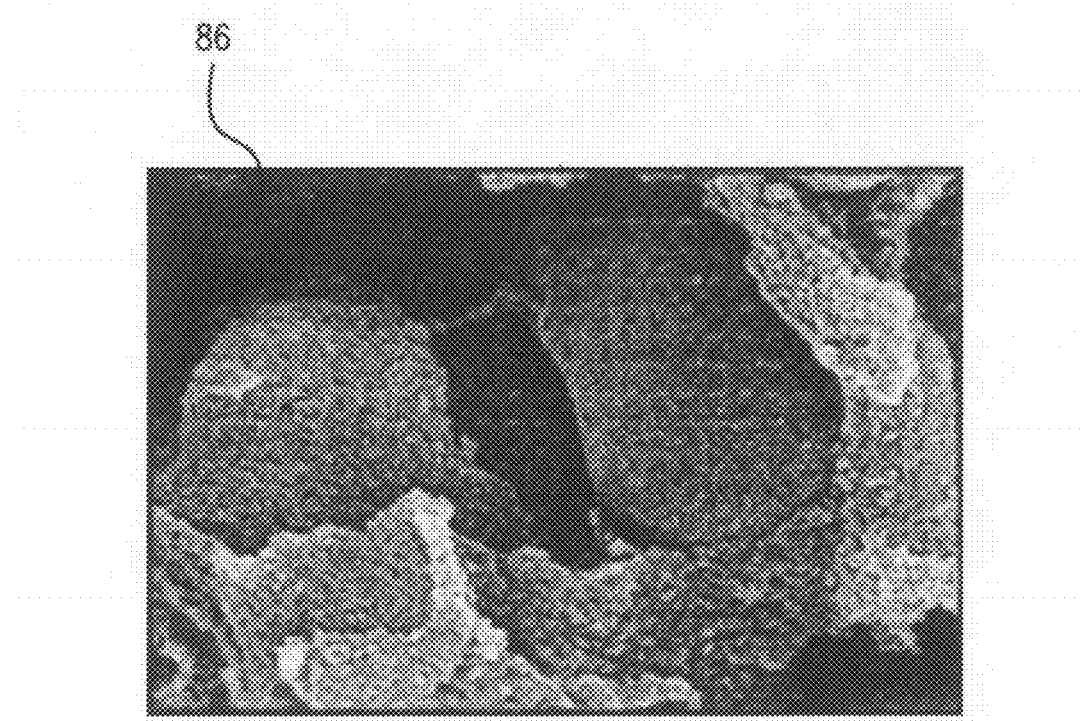
FIG. 12 is an enlarged view of a portion of the scanning electron microscope image of a natural protein ECM shown in FIG. 11.

Referring now to FIGS. 11-12, the protein matrix 86 that is formed from the platelet-rich blood product composition is shown. The matrix is composed of highly concentrated plasma proteins like VN and FN. FN is an ECM glycoprotein, which interacts with cells and alters their capacity to adhere, migrate and proliferate. FN is important for tissue development and maintenance and appears to serve as a scaffold for the deposition of Type I, Type III and Type IV collagen.

The protein matrix 86 forms complexes with various growth factors. The growth factors include VN, IGF, and IGFBPs that markedly enhance growth factor activity.

The protein matrix 86 entraps various growth factors, newly cultured dermal papilla, and keratinocytes to promote angiogenesis and mitogenesis. The growth factors also stimulate the activated stem cells, so that the activated stem cells attach to the protein matrix-growth factor complex to proliferate within the treatment area. Preferably, the platelet-rich blood product composition includes PDGF.

The main function of PDGF is to stimulate cell replication (mitogenesis) of the healing capable stem cells 50 shown in FIGS. 5-6. PDGF also stimulates cell replication of endothelial cells, which causes the budding of new capillaries into the wound (angiogenesis). The budding of new capillaries is a fundamental part of wound healing. PDGF also promotes the migration of perivascular healing-capable cells into the wounds 48 shown in FIGS. 5-6 and modulates the effects of other growth factors.

Many growth factors, such as PDGF, VEGF, IGF, epidermal growth factor (EGF), keratinocyte growth factors (KGF), and other similar growth factors, are essential to hair canal formation. Optionally, the growth factors are mixed with implantable cells that are mixed with the platelet-rich blood product composition for implantation into the treatment area.

Implantable cells include hair cells and stem cells that are harvested from any suitable source. Suitable sources include peripheral blood, adipose (fat) tissues, and bone marrow. Preferably, the implantable cells include cells harvested from autologous tissues in multiple follicular units, such as keratinocyte stem cells, dermal papilla cells, bulge stem cells, and epithelial stem cells.

The implantable cells are harvested from the sources and implanted into the subject using any suitable methods and equipment. Suitable methods and equipment for harvesting cells from adipose tissue include the LipiVage™ fat harvest, wash, and transfer system provided by Genesis Biosystems of Lewisville, Tex. Suitable equipment for harvesting cells from bone marrow include the SmartPReP 2 BMAC™ from Harvest Technologies Corporation of Plymouth, Mass. Other suitable methods for harvesting and implanting cells are disclosed in PCT Patent Publication Nos. 2007/035634 and 2007/062386, but the selection of a particular method is not critical.

Figure 13:
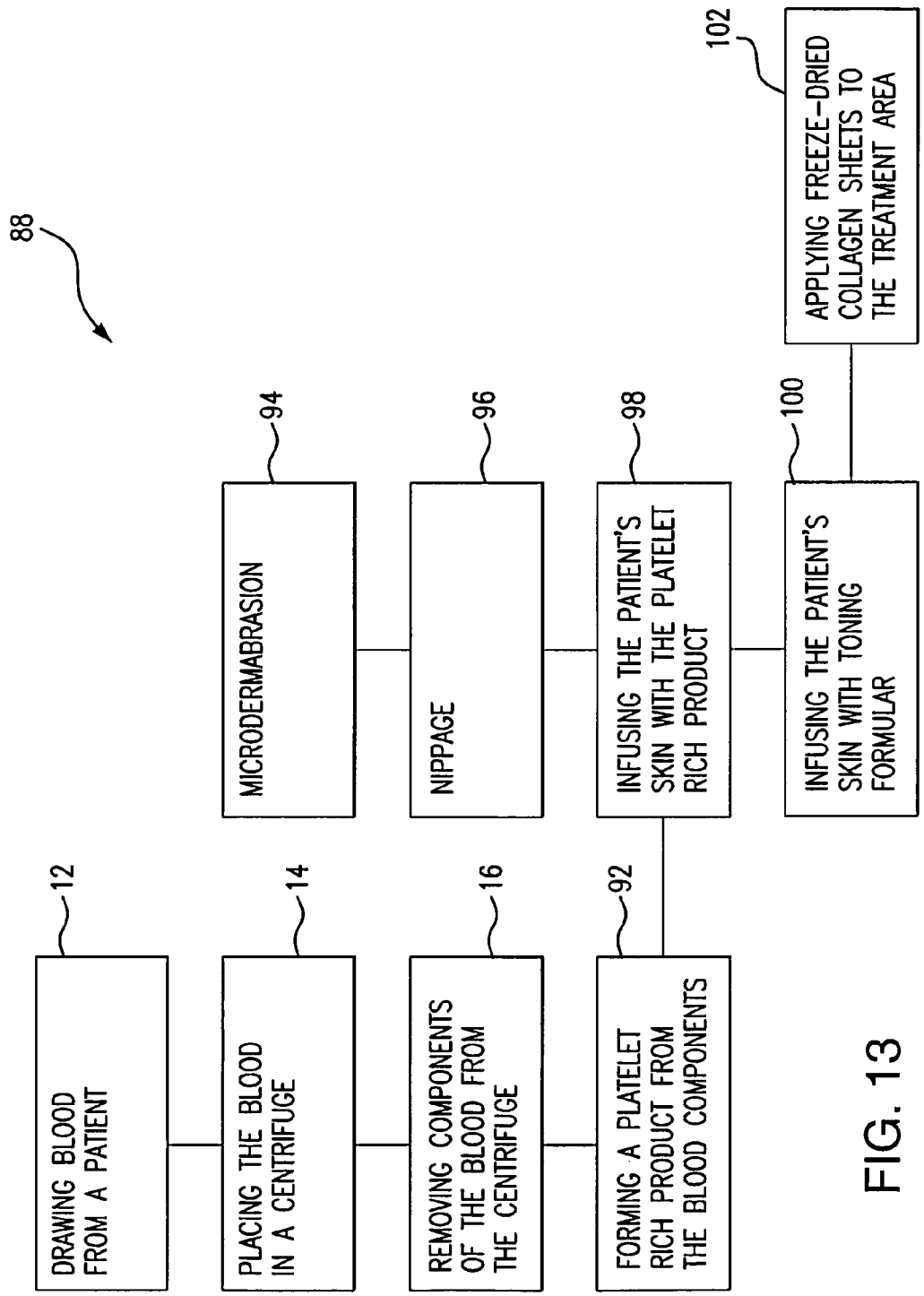
FIG. 13 is a block diagram for another embodiment of a skin treatment method includes traumatizing a treatment area and infusing a platelet-rich blood product composition into the treatment area.
Figure 14:
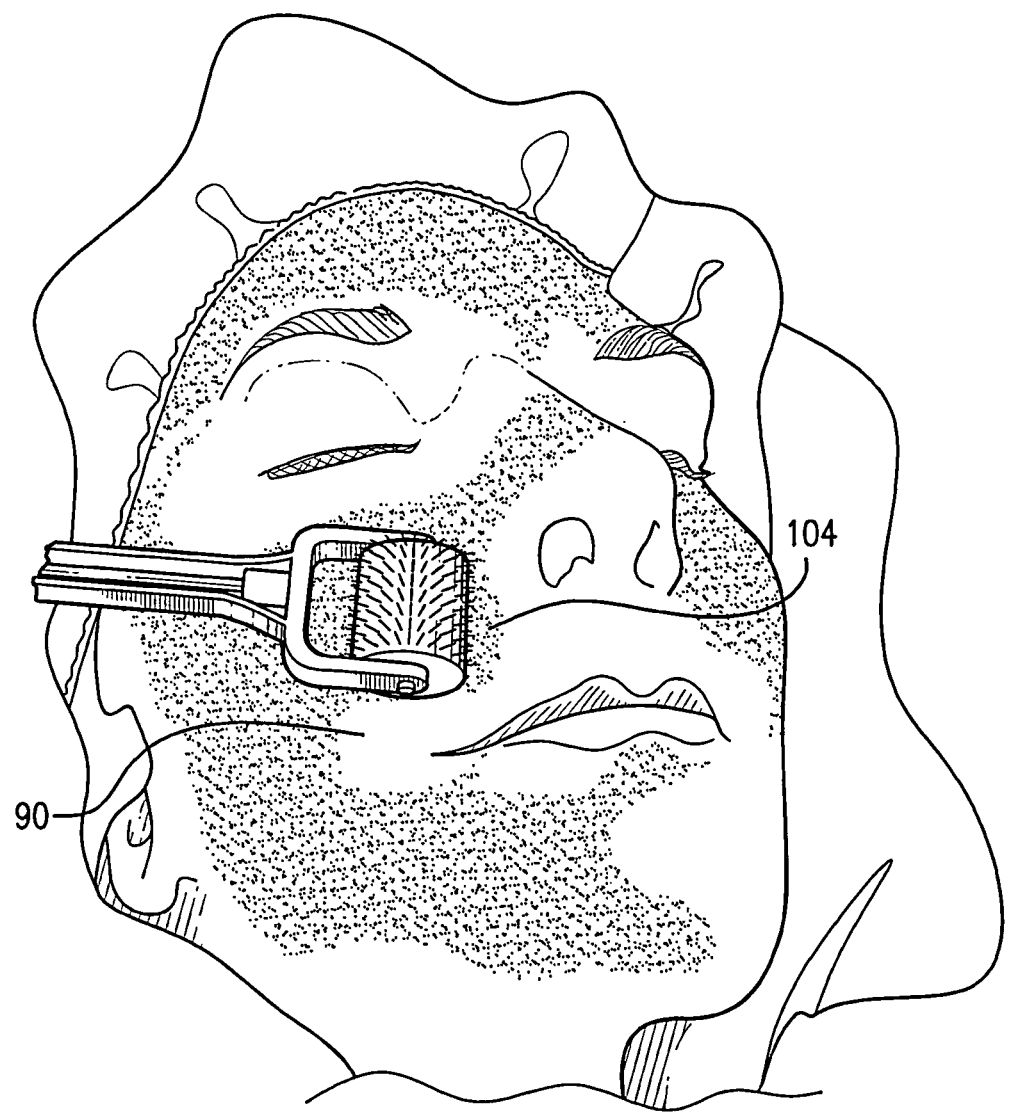
FIG. 14 is a perspective view of a human face being subjected to a skin treatment with the apparatus shown in FIG. 13.
Figure 15:
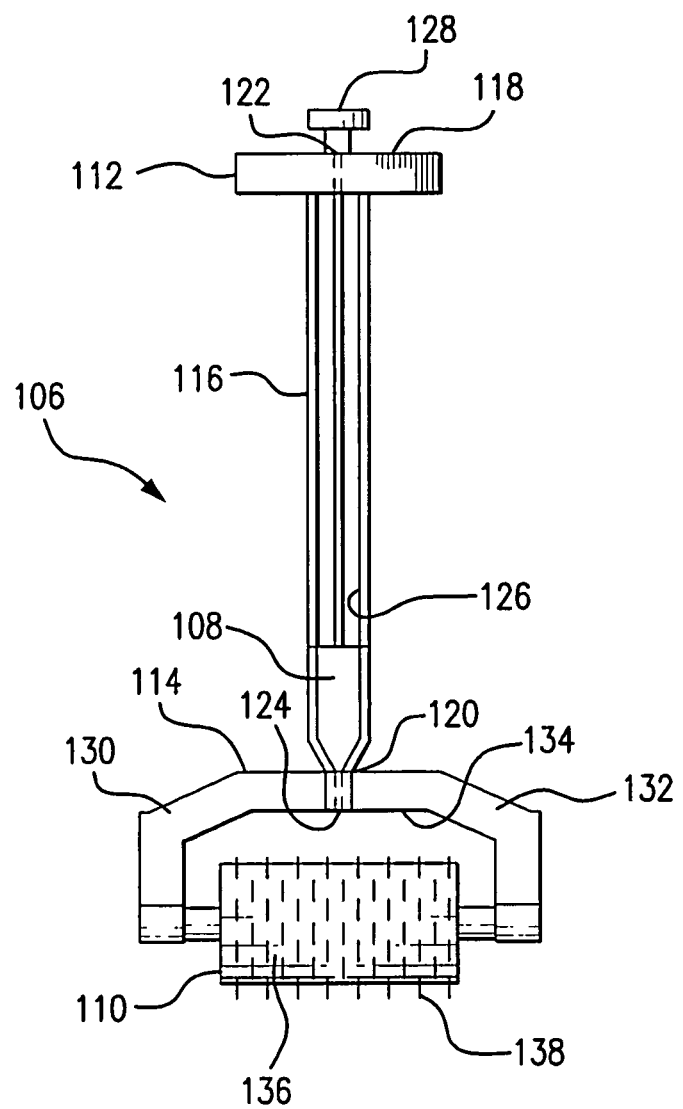
FIG. 15 is a view in side elevation of an apparatus for treating skin that includes a micro needling roller at one end and a container for dispensing platelet-rich blood product at the opposite end.

Referring now to FIGS. 13-15, there is shown another embodiment of a method for treating skin generally designated by the numeral 88. The method 88 is suitable for promoting hair growth on the scalp. The method 88 is also suitable for promoting collagen synthesis on other areas of the body, such as the face 90, as shown in FIG. 14.

The method 88 includes a series of steps 12, 14, 16, 92 directed to processing blood from a patient to obtain the platelet-rich blood product composition in the manner disclosed in FIGS. 1-12. The method 88 also includes a series of steps 94, 96, 98, 100, 102 directed to skin rejuvenation through the infusion of the composition into a traumatized region 104 shown in FIG. 14.

Unlike the embodiment shown in FIGS. 1-12, the step 92 involves loading the platelet-rich blood product composition into a traumatizing instrument 106 shown in FIG. 15. The traumatizing instrument 106 includes a container 108 for holding the platelet-rich blood product composition and a roller 110 for traumatizing skin. The container 108 dispenses the platelet-rich blood product composition onto the treatment area in step 98.

Referring to FIG. 13, the patient undergoes microderbrasion in step 94 to remove the stratum corneum in the treatment area. Preferably, the step 94 is performed while the platelets are being separated to form the platelet-rich blood product composition in steps 14, 16, 92. The microderbrasion in step 94 prepares the skin surface for the infusion of the platelet-rich blood product composition in step 98.

In the next step 96, the treatment area 104 shown in FIG. 14 undergoes nappage. Preferably, the nappage step 96 is performed using medical micro needle therapy. Micro needling is an effective, versatile, cost effective delivery system that allows the physician to induce collagen synthesis by infusing any variety skin toning substances, including platelet-rich plasma, concentrated platelet-poor plasma, or a platelet-rich blood product composition that includes a combination of both. CET is an effective adjunctive treatment that can be used in conjunction with many of the other non-surgical protocols such as botox and fillers for facial rejuvenation and skin enhancement.

As indicated in FIGS. 13-15, the platelet-rich blood product composition is infused into the treatment on the face 90 in step 98. Optionally, the nappage step 96 is continued with the roller 110 for the CET treatment.

The next step 100 involves applying a suitable toning formula to the patient's skin. Optionally, the toning formula is applied with hyaluronic acid. While the toning step 100 is being performed, freeze-dried collagen sheets are moistened for application in step 102.

The freeze-dried collagen sheets are moistened using any suitable solution, such as platelet-rich blood product composition, platelet-rich blood product, concentrated platelet-poor plasma, saline, a toning formula, or a combination thereof. Preferably, the collagen sheets are provided by Reviva Labs of Haddonfield, N.J.

Referring to FIGS. 13-14, the collagen sheets are applied to the treatment area 104 for a suitable time period in step 102. The collagen sheets hydrate the skin and infuse the platelet-rich plasma or toning formula into the micro channels. The channels close within an hour entrapping the platelet-rich plasma or toning formula beneath the epidermis. The high concentration of growth factors entrapped in the micro channels after the epidermis closes, accelerate wound healing cascade, which leads to skin remolding. Preferably, the collagen sheets are applied for thirty minutes.

Referring now to FIG. 15, the traumatizing instrument 106 includes an upper portion 112 for holding and dispensing the platelet-rich blood product composition and a lower portion 114 for traumatizing the treatment area 104 shown in FIG. 14 and infusing the platelet-rich blood product composition into the treatment area 104 in the infusion step 98 shown in FIG. 13.

The traumatizing instrument 106 includes an elongated member 116 that extends from the upper portion 112 to the lower portion 114. The elongated member 116 is tubular and includes an upper end 118 and a lower end 120. The upper end 118 includes an opening 122. The lower end 120 includes an opening 124. The openings 122, 124 communicate with one another through a connecting cavity 126.

The cavity 126 defines a chamber for holding the platelet-rich blood product composition. The cavity 126 receives the platelet-rich blood product composition through the first opening 122 and dispenses the platelet-rich blood product composition through the second opening 124. Preferably, the traumatizing instrument 106 includes a plunger 128 that inserts into the first opening 122 forming a syringe.

As shown in FIG. 15, the elongated member 116 includes a pair of tines 130, 132 that extend from the lower end 120 to define a fork 134. The fork 134 receives the roller 110 that is mounted for rotation therein. The roller 110 includes a rotating surface 136 with a plurality of protrusions 138. Preferably, the protrusions 138 include microneedles.

In operation, the roller 110 rotates the surface 136 to traumatize the treatment area 104 shown in FIG. 14 with the protrusions 138 to form activated stem cells therein. The plunger 128 inserts into the first opening 122 and moves in a vertical direction to force the platelet-rich blood product composition through the second opening 124 onto the treatment area. Preferably, the second opening 124 is in overlying relation with the roller 110, so that the platelet-rich blood product composition is directed onto the roller surface 136 with the protrusions 138 injecting the platelet-rich blood product composition into the treatment area.

It should be understood that the traumatizing instrument 106 shown in FIG. 15 is suitable for use with the method 10 shown in FIGS. 1-12.

It should also be understood that the method 10 shown in FIG. 1 is also suitable for use in hair transplant surgery by applying the platelet rich blood product composition in the donor area to enhance wound repair, to decrease scar collagen, to enhance Type III collagen, and to increase wound tensile strength.

It should also be understood that the platelet-rich blood product composition is suitable for use as a graft storage medium to increase graft yield and is injected into the recipient site to revascularize the recipient area to increase the yield of the transplanted follicular grafts and reverse the effects of hair miniaturization in the non transplanted hair.

It should also be understood that the methods are suitable for hair multiplication. The method are not limited to combining newly cultured dermal papilla and keratinocytes with the platelet rich concentrate mixture prior to infusion into scalp. The method is also suitable for use prior to the infusion of cultured dermal papilla cells and keratinocytes or for the placement of proto-hairs with or without a biological matrix.

The present invention is further illustrated through the following non-limiting example.

EXAMPLE 1

In that study, ten hair samples were taken from each patient, 5 patients in the control group and 5 patients from the treatment group. Ten hair samples were taken because of the ratio of 90% antigen and 10% telogen hairs and hair diameter was measured with a Starrett micrometer one cm above the base.

All patients were administered local anesthesia in the treatment area. The treatment group included five patients. From each patient, 60 cc of blood was drawn to produce 10 cc of platelet-rich plasma. The control group of patients also had 60 cc of blood drawn, but this was not processed. Local anesthesia was use in both groups.

The scalp was first traumatized in both the treatment group and the control group with a 1 mm micro needling roller to initiate the Stat3-dependent keratinocyte migration towards the antigen progression and wound healing. Then, the treatment group was injected with platelet-rich plasma in a retrograde fashion "deep to superficial" every cm throughout the treated area and then platelet-rich plasma was sprayed on the scalp and left on over night. Normal saline was injected into the scalp of the control group in a similar fashion.

Patients were evaluated and hair diameter measurements were taken by micrometer at 4 months and 8 months post treatment in a similar fashion and an average of 10 hairs were measured and compared. The results revealed an increase of 9.7% in average hair shaft diameter at 4 months and then 6.1% at 8 months in the Treatment Group. The Control Group demonstrated a 2.8% average decrease in hair shaft diameter at 4 months and 3.5% decrease at 8 months.

The average hair shaft diameter for the treatment group increased dramatically within four months and then gradually decreased at eight months, due to the effects of DHT. The average hair shaft diameter for the control group decreased dramatically for the first four months and continued to decrease from four months to eight months.

EXAMPLE 2

Hair growth was stimulated in an Alopecia Areata patient after traumatizing and infusing platelet rich concentrate. The patient was growing hair at one month and hair growth continued over twelve months and only one treatment.

According to the provisions of the patent statutes, we have explained the principle, preferred construction and mode of operation of our invention and have illustrated and described what we now consider to represent its best embodiments. However, it should be understood that, within the scope of the appended claims, the invention may be practiced otherwise than as specifically illustrated and described.

We claim:

1. A method for promoting hair growth within skin that includes a plurality of hair follicles comprising:
    obtaining a volume of a platelet-rich blood product composition from a volume of anti-coagulated blood to include a natural protein extra cellular matrix containing growth factors,
    traumatizing a portion of the bald area of scalp of a human patient containing hair follicles within a treatment area of the scalp to activate stem cells within the hair follicles to form a quantity of activated stem cells within the treatment area, and
    infusing the natural protein extra cellular matrix containing growth factors into the treatment area to interact with the activated stem cells to form a complex between the protein extra cellular matrix of growth factors and the activated stem cells so that the activated stem cells proliferate within the treatment area to grow new hair follicles.

2. A method as set forth in claim 1 wherein the traumatizing further includes:
    traumatizing a portion of the scalp with a trauma instrument selected from the group consisting of a mechanical incision trauma instrument, a micro needling roller, a laser, a light source, a photo therapy instrument, an ultrasonic instrument, an electroportation instrument, an epidermal abrasion instrument, a dermal abrasion instrument, a heater, a cooler, a chemical dispenser, a liquid dispenser, a gel dispenser, a lotion dispenser, a cream dispenser, a gas dispenser, a vapor dispenser, and a naturopathic chemical dispenser.

3. A method as set forth in claim 1 wherein the infusing further includes:
    infusing the natural protein extra cellular matrix containing growth factors concentrated protein matrix into the treatment area through a technique selected from the group consisting of injection, micro needling, ultrasound, electroportation, transdermal infusion, patching, dressing, vacuum assisted infusion, mechanical infusion, chemical infusion, and mineral infusion.

4. A method as set forth in claim 1 wherein the obtaining further includes:
    separating a volume of platelet-rich plasma from the volume of anti-coagulated blood,
    forming the platelet-rich blood product composition with a preselected volume of platelet-rich plasma
    separating a volume of concentrated platelet poor plasma from the volume of anti-coagulated blood, and
    mixing the volume of concentrated platelet poor plasma with the platelet-rich plasma to form the platelet-rich blood product composition.

5. A method as set forth in claim 1 wherein the obtaining further includes:
    placing a volume of anticoagulated blood into a centrifuge machine and centrifugally separating the volume of blood, at a first speed, into a platelet poor plasma component, a buffy coat component, and a layer of red blood cells, the buffy coat component comprising platelets,
    transferring the platelet poor plasma component from the volume of blood to a first collection device,
    extracting additional platelets from the red blood cell layer into the buffy coat component to form a concentrated platelet-rich plasma component,
    hemoconcentrating the concentration of platelets within the platelet poor plasma component to produce a concentrated platelet-poor plasma component, and combining the concentrated platelet-poor plasma component with the concentrated platelet-rich plasma component to form the platelet-rich blood product composition.

6. A method as set forth in claim 1 wherein the infusion further includes:

combining the natural protein extra cellular matrix with implantable cells selected from the group consisting of implantable hair cells, implantable stem cells, and both implantable hair cells and implantable stem cells to form a mixture of the platelet-rich blood product composition and the implantable cells, and applying the mixture to the treatment area to infuse the natural protein extra cellular matrix with implantable cells into the treatment area.

7. A method as set forth in claim 1 wherein the traumatizing and infusing further include:

providing an elongated member having a container for holding the platelet-rich blood product composition at one end and a roller with a plurality of protrusions for traumatizing the treatment area of the scalp extending from the opposite end, rotating the roller on the treatment area to traumatize the treatment area, and dispensing the platelet-rich blood product composition from the container to infuse the platelet-rich blood product composition into the treatment area.

* * * * *